(12) United States Patent
Krüger

(10) Patent No.: US 7,018,413 B2
(45) Date of Patent: Mar. 28, 2006

(54) MODULAR SYSTEM FOR SPINAL COLUMN FUSION

(75) Inventor: Manfred Krüger, Arnoldshain (DE)

(73) Assignee: Tutogen Medical GmbH, Neunkirchen and Brand (DE)

( * ) Notice: Subject to any disclaimer, the term of this patent is extended or adjusted under 35 U.S.C. 154(b) by 0 days.

(21) Appl. No.: 10/493,341

(22) PCT Filed: Aug. 28, 2002

(86) PCT No.: PCT/EP02/09602

§ 371 (c)(1),
(2), (4) Date: May 26, 2004

(87) PCT Pub. No.: WO03/034956

PCT Pub. Date: May 1, 2003

(65) Prior Publication Data

US 2004/0267366 A1    Dec. 30, 2004

(30) Foreign Application Priority Data

Oct. 24, 2001   (DE) ................ 101 52 567

(51) Int. Cl.
*A61F 2/44* (2006.01)
(52) U.S. Cl. .................................. 623/17.11
(58) Field of Classification Search ............ 623/16.11, 623/17.11, 17.15, 17.16, 23.47; 606/61
See application file for complete search history.

(56) References Cited

U.S. PATENT DOCUMENTS

| 5,397,364 | A | * | 3/1995 | Kozak et al. ............. 623/17.11 |
|---|---|---|---|---|
| 6,025,538 | A | | 2/2000 | Yaccarino, III .............. 623/16 |
| 6,174,311 | B1 | | 1/2001 | Branch et al. ................. 606/61 |
| 6,200,347 | B1 | * | 3/2001 | Anderson et al. ......... 623/16.11 |
| 6,258,125 | B1 | * | 7/2001 | Paul et al. ................ 623/17.11 |
| 6,368,351 | B1 | * | 4/2002 | Glenn et al. ............. 623/17.15 |
| 6,468,311 | B1 | * | 10/2002 | Boyd et al. .............. 623/17.16 |
| 6,656,178 | B1 | * | 12/2003 | Veldhuizen et al. .......... 606/61 |
| 6,685,742 | B1 | * | 2/2004 | Jackson .................... 623/17.11 |
| 6,719,794 | B1 | * | 4/2004 | Gerber et al. ............ 623/17.11 |
| 6,743,256 | B1 | * | 6/2004 | Mason ..................... 623/17.16 |
| 2002/0029082 | A1 | * | 3/2002 | Muhanna ................. 623/17.11 |
| 2002/0029084 | A1 | * | 3/2002 | Paul et al. ............... 623/23.63 |
| 2002/0055781 | A1 | * | 5/2002 | Sazy ....................... 623/17.11 |
| 2003/0036798 | A1 | * | 2/2003 | Alfaro et al. ............ 623/17.16 |

FOREIGN PATENT DOCUMENTS

| DE | 297 20 022 U1 | 11/1997 |
|---|---|---|
| DE | 299 13 200 U1 | 7/1999 |
| DE | 199 52 939 A1 | 11/1999 |
| EP | 0 298 235 | 5/1988 |
| WO | 01/64141 A1 | 9/2001 |
| WO | 01/70137 A2 | 9/2001 |

OTHER PUBLICATIONS

"Anatomic Considerations for Anterior Instrumentation of the Lubar Spine", Ebraheim et al., Orthopedics, Oct. 1999, vol. 22, No. 10.

* cited by examiner

*Primary Examiner*—Eduardo C. Robert
*Assistant Examiner*—David Cornstock
(74) *Attorney, Agent, or Firm*—Gifford, Krass, Groh, Sprinkle, Anderson & Citkowski, P.C.

(57) ABSTRACT

The invention relates to a spinal implant consisting of a bone material body which is embodied in a curved manner in its longitudinal direction and is provided with coupling means.

14 Claims, 3 Drawing Sheets

Fig. 1
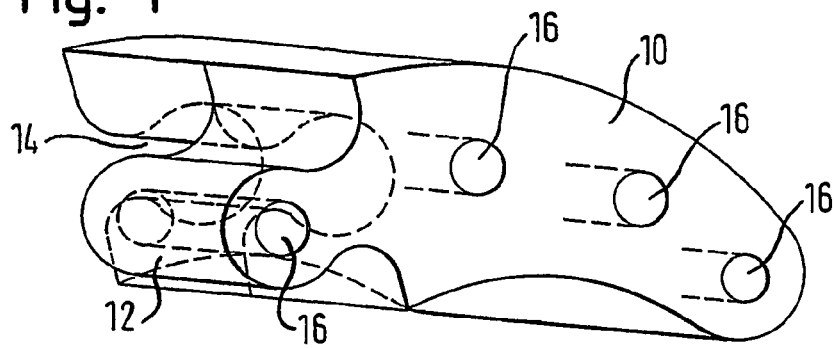
Fig. 2
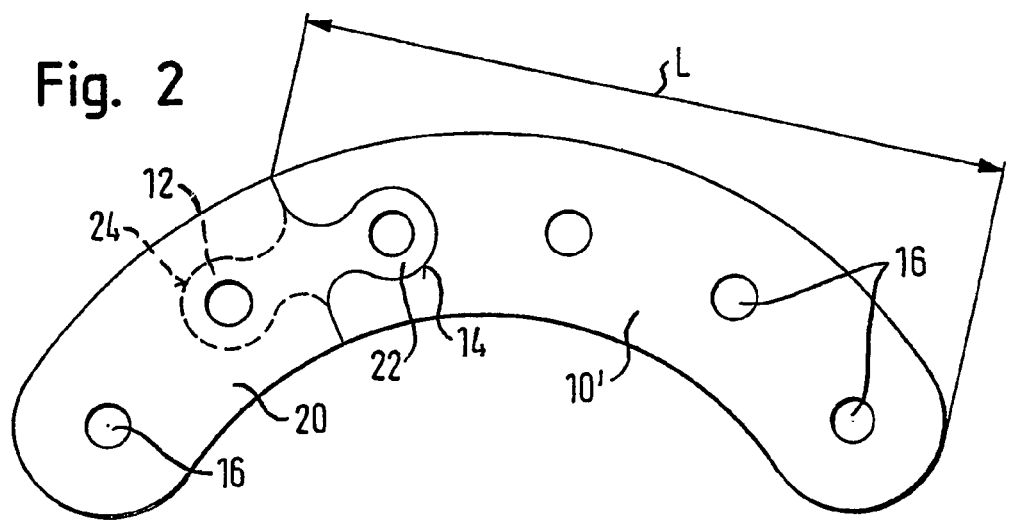
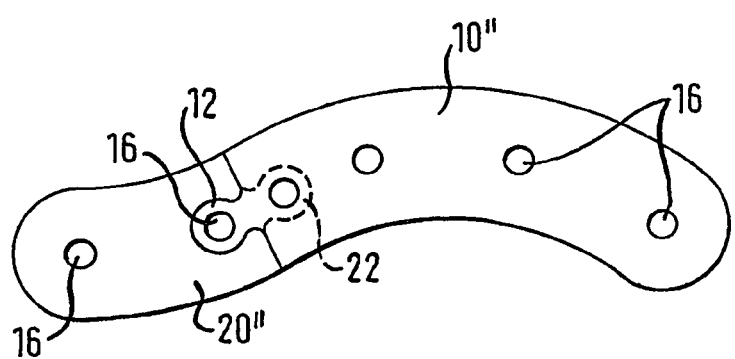
Fig. 3
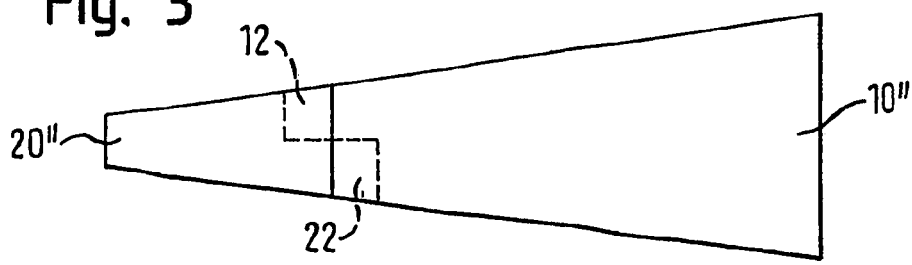

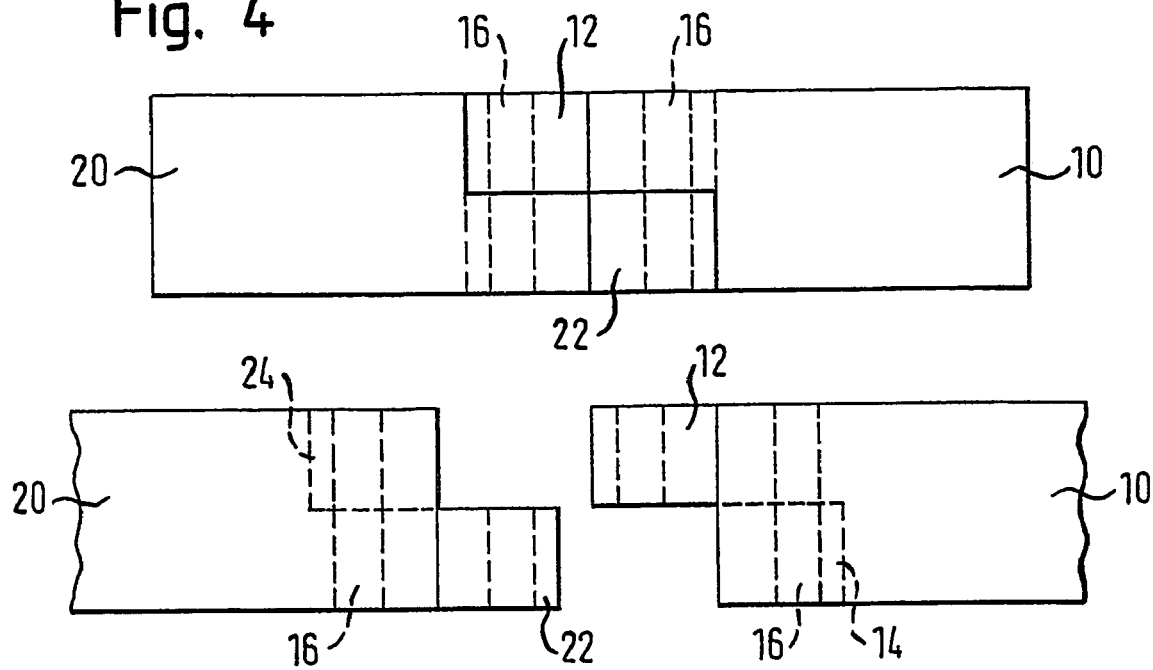
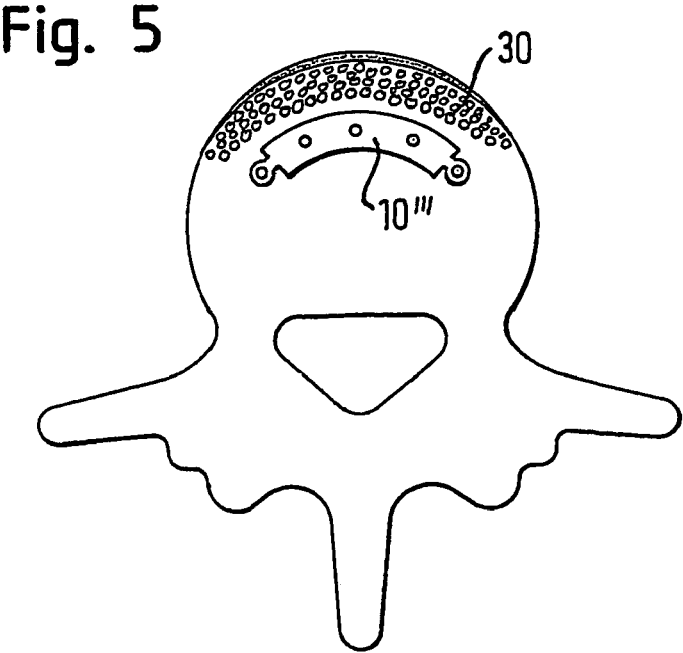

MODULAR SYSTEM FOR SPINAL COLUMN FUSION

RELATED APPLICATIONS

This application is the U.S. National Phase of PCT Application PCT/EP02/09602 filed Aug. 28, 2002, which claims priority of German Application DE 101 52 567.2 filed Oct. 24, 2001, the contents of which are herein incorporated by reference.

FIELD OF THE INVENTION

The present invention relates to a spinal implant for interbody fusion to the spinal column.

BACKGROUND OF THE INVENTION

The degeneration of the intervertebral disk, in particular of the nucleus pulposus, results in a loss of height in the affected disk space which is associated with a weakening of the annulus fibrosus and of the ligaments. The spinal column hereby becomes instable at this position. The consequence is a horizontal displaceability of the vertebral bodies with respect to one another which results in impairments of the nerve roots in this region and/or of the spinal marrow with pain resulting therefrom.

The principle for the treatment of these symptoms consists of the surgical removal of the nucleus pulposus and the insertion of support bodies in order to restore the normal height of the disk space.

There is a variety of demands on spinal implants, and in particular on implants for interbody fusion of the lumbar vertebral column. For instance, on the one hand, a contact surface with the vertebral bodies to be fused should be provided which is as large as possible. This means that, if conventional implants are used, a plurality of implants have to be kept in stock since the required dimensions cannot be determined precisely pre-operatively and since the length and the height of the vertebral bodies varies. Studies have namely shown that the length of the vertebral bodies can fluctuate between 22 and 34 mm and their width can fluctuate between 31 and 49 mm (cf. Ebraheim et al, Anatomic Considerations for Anterior Instrumentation of the Lumbar Spine, ORTHOPEDICS, October 1999, Volume 22 No. 10).

A further demand on spinal implants, and in particular on implants for the lumbar vertebral column, is sufficient and sufficiently predictable compression strength. Furthermore, the spinal implant should, where possible, have the same resilience as the bone, which is not the case with conventional metal implants.

A spinal implant for interbody fusion to the spinal column is known from DE 199 52 939 A1 which consists of a body made from bone material which is curved in the direction of its longitudinal extent.

SUMMARY OF THE INVENTION

It is the object of the invention to further develop such a spinal implant such that the demands initially named are satisfied and such that in particular the number of implant bodies to be kept in stock can be reduced.

This object is satisfied by the present invention and in particular in that at least one coupling means is provided at at least one end of the body which is made in one piece with the body and which serves for the coupling to an extension part provided with a complementary coupling means in order to extend the spinal implant in the direction of its longitudinal extent.

In accordance with the invention, the spinal implant is made as a base body which has a coupling means in order to couple an extension part likewise consisting of bone material. A plurality of implant designs can be achieved with the aid of the base body in accordance with the invention by the provision of extension parts of different length and/or curvature, with a small number of implant bodies to be kept in stock.

Advantageous embodiments of the invention are described in the description, in the drawing and in the dependent claims.

In accordance with a first preferred embodiment, the body, and in particular also the extension part, are composed cortical bone material. In contrast to the ileac wedges usually used, they have a uniform compression strength per surface unit of cross-section.

In accordance with a further preferred embodiment, the coupling means can be made for shape matched connection to the complementary coupling means. It is hereby possible to connect both the body and the extension part to one another by a simple plugging together of the coupling means, with a reliable and firm connection nevertheless being ensured which cannot release under its own power after implanting.

In accordance with a further preferred embodiment, a first coupling means and a second coupling means are provided at at least one end of the body. More particularly, one coupling means is made as a projection and one coupling means is made as a cut-out. In this embodiment, both a projection and a cut-out are located at one end of the body, with a complementary projection and a complementary cut-out being able to be provided at the associated end of the extension part such that the body and the extension part are connected in a shape matched manner and fixedly to one another by a simple plugging into one another.

A respective first coupling means and a second coupling means are preferably provided at each of the two ends of the body, with one coupling means being made as a projection and one coupling means being made as a cut-out. More preferably, the projection and the cut-out at one end of the body can be arranged in different longitudinal planes of the body. In this embodiment, a universal use of the body is possible, on the one hand, since it can be provided with extension parts at both its ends. On the other hand, a particularly stable connection is provided since the projection and the cut-out are arranged in different planes of the body.

A further aspect in accordance with the one invention is the combination of a spinal implant with an aforesaid base body and an extension part made of bone material which is provided with at least one further complementary coupling means. The curvature of the body can merge constantly into the curvature of the extension part when the body and the extension part are connected to one another. As required, the curvature can extend continuously or with a changing sign, that is circular segments or also S-shaped implants can be provided by using different extension parts.

The body and/or the extension part preferably has/have a rounded end. Alternatively, the body can be provided with a projection at one end or at both ends. If the base body is used without an extension part, it is possible either to leave the projection as is or, however, to remove it by sawing or in another manner.

Both the body and the extension part can be either planoparallel or, however wedge-shaped or trapezoid in cross-section. With a wedge-shaped or trapezoid shape, the bending in a ring segment shape can be made either radially or along the longest secant. With an S-shaped extension, the wedge shape or trapeze shape is preferably made along the longitudinal edge of the S, with the highest point lying at the rounded end of the base member. The wedge shape or trapeze shape preferably continues beyond the extension pieces.

With a ring-shaped extension, the chamfering can be made in the radial direction, with the highest point lying at the center of the outer periphery of the ring segment. In this case, the body can be provided in each case with a projection at its ends, with the extension pieces to be applied to both sides following the tapering accordingly.

In accordance with a further preferred embodiment, the first coupling means and the second coupling means substantially have the same height, which preferably amounts to half the height of the body. A particularly stable connection is hereby created between the body and the extension part.

The outer radius of the body curved in its longitudinal extent can amount to at least 12 mm, with its height being able to amount to approximately 6 to 18 mm.

Both the base body and the extension part can be smooth or roughened at their lower sides and/or upper sides, with the roughening being able to be of a ribbed or napped type, The ribs or naps can be either blunt or also sharp-edged or acute.

In accordance with a further preferred embodiment, both the base body and the extension part can be provided with vertical openings which promote the ingrowth of bone callus or which can be filled with autologous, allogenic or xenogenic bone replacement material or growth-promoting material. The shape of these openings can generally be any desired, but preferably circular in the sense of a bore.

In accordance with a further aspect, the invention relates to a modular system for interbody fusion to the spinal column which consists of at least one aforesaid base body and a plurality of extension parts which are each provided with a further complementary coupling means, with the extension parts having different lengths and/or curvatures.

Spinal implants of the most varied dimensions and designs can be put together by such a modular system, without a correspondingly large number of implants having to be kept in stock, since the respectively required shape and size can be matched by putting together a corresponding base body and extension part(s).

The present invention will be described in the following purely by way of example with reference to advantageous embodiments and to the enclosed drawings. There are shown:

BRIEF DESCRIPTION OF THE DRAWINGS

FIG. 1 shows a perspective view of an embodiment of a base body according to the present invention;

FIG. 2 shows a plan view of an alternate base body which is connected to an extension part;

FIG. 3 shows a plan view and a side view of another alternate base body with a connected extension part with a wedge-shaped cross-section;

FIG. 4 shows an enlarged side view of the coupling means of a base body and of the extension part; and FIGS. 5 to 8 show different applications for the implanting of a spinal implant in accordance with the invention into a disk space.

DETAILED DESCRIPTION OF THE PREFERRED EMBODIMENTS

Figure 6:
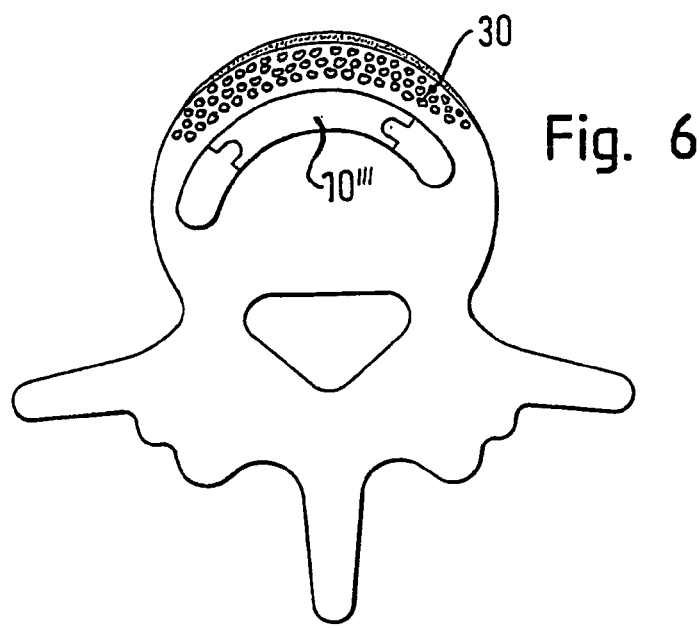

FIG. 1 shows a perspective, schematic view of a spinal implant in accordance with the invention for interbody fusion to the spinal column which consists of a body or base body 10 made of bone material which is generally elongate and is curved in the direction of its longitudinal extent. The base body is cut out of a sufficiently thick bone of human or animal origin as a ring segment, with the width of the ring segment having to amount to at least 4 mm and the outer radius of the ring segment having to amount to at least 12 mm. The height of the segment or of the base body can lie between 6 and 18 mm.

As FIG. 1 shows, two coupling means are provided in the form of a projection 12 and of a cut-out 14 at the end of the base body 10 at the left in FIG. 1. Both the height of the projection 12 and the height of the cut-out 14 amount to half the height of the base body 10. The projection 12 is spigot-like and is connected to the base body 10 in one piece. The shape of the projection 12 can generally vary, for example be dove-tail shaped or oval. The spigot is, however, preferably circular in its cross-section, with the rounding of the neck preferably having the same radius as the projection itself. The cut-out 14 is made complementary to the projection, that is it is likewise circular and has a neck which has the same radius as the rounding of the cut-out.

The end of the base body 10 at the right in FIG. 1 is rounded, preferably in the shape of a semi-circle. Alternatively, however, coupling means, that is projections and cut-outs, can be provided at both ends at the base body.

Furthermore, the base body 10 is provided with vertically throughgoing bores 16 which are distributed over the longitudinal extent of the base body 10. As FIG. 1 shows, a total of four bores 16 are provided in the base body 10, with one being located at the center of the projection 12.

FIG. 2 shows a plan view of a further embodiment of a base body 10'. This base body 10' is substantially made in precisely the same manner as the base body 10, with the position of the projection 12 and of the cut-out 14, however, being swapped over, that is the projection 12 is provided at the lower side of the base body 10' and the cut-out 14 is provided at the upper side of the base body 10'.

The base body 10' is furthermore connected to an extension part 20 which is provided with complementary coupling means, that is likewise with a projection 22 and with a recess 24, with the projection 22 and the recess 24 being arranged such that the base body 10' and the extension part 20 can be plugged into one another in shape matched manner.

As FIG. 2 shows, a spinal implant is created overall which is made in ring segment shape and which is rounded in a circular manner at its ends. Furthermore, a total of six throughgoing bores are located at the center of the combined spinal implant and are uniformly spaced apart over the longitudinal extent of the spinal implant. The longitudinal extent L of the base body 10' amounts to approximately 18 mm between the points of the full body spaced furthest apart in a straight line. In the extension part 20, the distance between the points of the full body furthest apart from one another amounts to approximately 4 mm up to approximately 12 mm. A plurality of extension parts are preferably provided, with the distance between the individual extension parts varying in steps of 4 mm.

The extension parts 20 are generally made with a rounded end. The end with the projection and the cut-out is preferably made in two variants, in which the position of the projection and the cut-outs is swapped over. It is hereby possible to extend the base body 10 with an extension part optionally in the shape of a ring segment or in S shape.

FIG. 3 shows a plan view of such an embodiment in which a base body is plugged together with an extension part to form an S shape. As the side view of FIG. 3 shows, in this embodiment, both the base body 10" and the extension part 20" are wedge-shaped in cross-section, with the outer contour of the assembled spinal implant extending constantly. In another respect, the same elements are provided with the same reference numerals.

FIG. 4 shows a side view of a base body 10 and of an extension part 20 in the state plugged together and in the state unplugged from one another. As can be recognized, the projections 12 and 22 of the base body 10 or of the extension part 20 each have a step which corresponds to half the height of the base body or of the extension part 20 in the region of the joint.

FIGS. 5 to 8 show different application examples of the spinal implant described above.

FIG. 5 shows a plan view of a vertebral body, with the transforaminal lumbar interbody fusion (TLIF) being shown. In this implanting technique, an intervertebral joint is removed and the foramen of the nerve root is thereby exposed. The removed disk space is filled with bone chips 30 in the anterior third. The implant in the form of a base body 10" slides into its position along these bone chips The base body 10" is generally designed as described above. However, in this embodiment, a coupling possibility is provided at both ends of the base body 10", that is a respective projection and a respective cut-out are arranged at both ends. If necessary, the projections at both ends of the base body 10" can be removed prior to implanting.

FIG. 6 shows a view similar to FIG. 5 of a TLIF, with an extension part, which is rounded in each case at its outer end, however, being provided at both ends of the base body 10".

Figure 7:
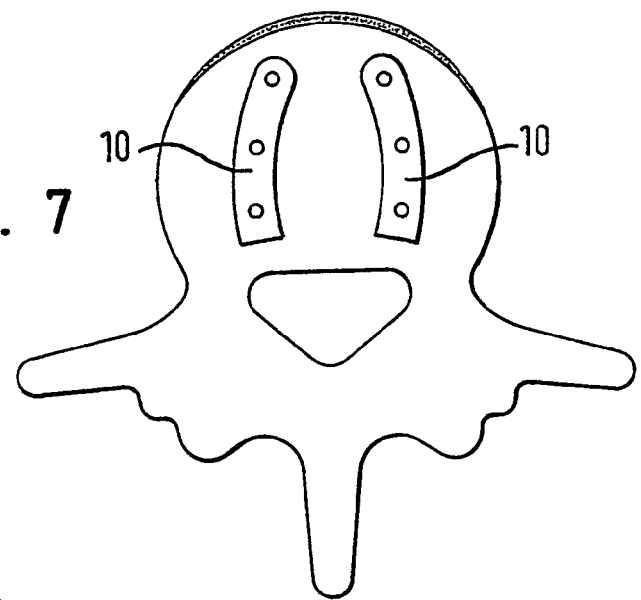

FIG. 7 shows an application example of posterior lumbar interbody fusion (PLIF) in which two implants made in the same manner are pushed into the disk space to the left and right respectively past the spinal marrow. In the example shown, there are two base bodies 10 in which the respective projections 12 have been removed.

Figure 8:
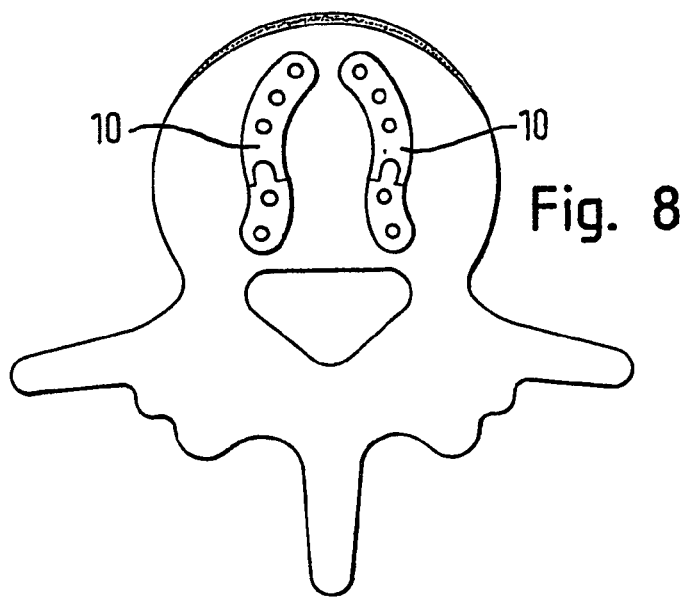

Finally, in FIG. 8, a further application example of a PLIF is shown in which the base bodies are respectively extended in an S shape by an extension part.

Generally, the human or animal bone used for the spinal implant in accordance with the invention is subjected to a sterilization process which makes viruses inactive prior to or after its processing into the shapes in accordance with the invention.

REFERENCE NUMERAL LIST

10, 10', 10", 10''' base bodies
12 projection
14 cut-out
20,20" extension part
22 projection
24 cut-out
30 bone chips

What is claimed is:

1. A modular system for interbody fusion to the spinal column comprising:
    at least one spinal implant having a body, the body having a height and a longitudinal extent, the body being made from bone material and having a curved form in the direction of the body longitudinal extent,
    wherein a first coupling has a first projection extending from one end of the body and is integrally formed with the body, and a first recess formed in the body at the one end of the body; and
    a plurality of extension parts, each of the plurality of extension parts having a second coupling that is engageable to the first coupling and that includes a second projection extending therefrom and a second recess formed therein, with the plurality of extension parts differing in a characteristic selected from the group consisting of: length, curvature, and a combination thereof.

2. The system in accordance with claim 1, characterized in that the body comprises cortical bone material.

3. The system in accordance with claim 1, characterized in that the first coupling means is made for shape matched connection to the complementary coupling means.

4. The system in accordance with claim 3, characterized in that a first coupling means and a second coupling means are provided at at least one end of the body, wherein the first coupling means is a projection and the second coupling means is a cut-out.

5. The system in accordance with claim 4, characterized in that the first and second coupling means are provided at each of the two ends of the body, and the first coupling means is made as a projection and the second coupling means is made as a cut-out, with the projection and the cut-out in particular being arranged in different longitudinal planes of the body.

6. The system in accordance with claim 4, characterized in that both the first coupling means and the second coupling means substantially have the same height.

7. The system in accordance with claim 6, characterized in that both the first coupling means and the second coupling means are each of a height of substantially half the height of the body.

8. The system in accordance with claim 1, characterized in that the curvature of the body merges constantly into the curvature of at least one of the plurality of the extension parts when the body and the at least one extension part are connected.

9. The system in accordance with claim 8, characterized in that at least one of the extension parts has a rounded end.

10. The system in accordance with claim 8, characterized in that both the body and at least one of the extension parts are wedge-shaped or trapezoidal in cross-section.

11. The system in accordance with claim 1, characterized in that at least one of the plurality of extension parts has a rounded end.

12. The system in accordance with claim 11, characterized in that both the body and at least one of the extension parts are wedge-shaped or trapezoidal in cross-section.

13. The system in accordance with claim 1, characterized in that the body and at least one of the plurality of extension parts are wedge-shaped or trapezoidal in cross-section.

14. The system in accordance with claim 1, characterized in that the body has an outer radius of at least 12 mm and the height is approximately 6 to 18 mm.

* * * * *